United States Patent [19]
Kato et al.

[11] Patent Number: 5,187,101
[45] Date of Patent: Feb. 16, 1993

[54] ELECTROLYTIC SOLUTION FOR KARL FISCHER'S COULOMETRIC TITRATION AND METHOD FOR MEASURING WATER CONTENT USING SAME

[75] Inventors: Hiromasa Kato, Tokyo; Yuka Fujimoto, Kanagawa; Akiyoshi Nozawa, Kanagawa; Shinichi Kuwata, Kanagawa, all of Japan

[73] Assignee: Mitsubishi Kasei Corporation, Tokyo, Japan

[21] Appl. No.: 704,510

[22] Filed: May 23, 1991

[30] Foreign Application Priority Data

Nov. 6, 1990 [JP] Japan .................. 2-300859

[51] Int. Cl.⁵ ............................................. G01N 33/18
[52] U.S. Cl. ..................................................... 436/42
[58] Field of Search ......................................... 436/42

[56] References Cited

U.S. PATENT DOCUMENTS

| 2,967,155 | 1/1961 | Blomgren et al. | 436/42 |
| 4,725,552 | 2/1988 | Dahms | 436/42 |

FOREIGN PATENT DOCUMENTS 2176294 12/1986 United Kingdom ............... 436/42

*Primary Examiner*—John W. Rollins
*Attorney, Agent, or Firm*—Sughrue, Mion, Zinn, Macpeak & Seas

[57] ABSTRACT

An electrolytic solution for Karl Fischer's coulometric titration comprising a iodide ion, sulfur dioxide, a basic compound and a solvent, and a method for measuring a water content using the same are disclosed. In the electrolytic solution, the basic compound is a mixture comprising an amino alcohol and a compound represented by formula (I):

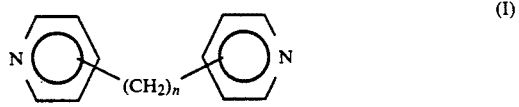

wherein n represents an integer of from 1 to 3, the amino alcohol is present at a molar ratio of not more than 1 to sulfur dioxide, and the amino alcohol and compound represented by formula (I) is present at a total molar ratio of from 1 to 5 to sulfur dioxide. The electrolytic solution is free from a pyridine odor, applicable either as an anolyte or as a catholyte, and capable of considerably reducing time required for water content measurement.

29 Claims, No Drawings

ELECTROLYTIC SOLUTION FOR KARL FISCHER'S COULOMETRIC TITRATION AND METHOD FOR MEASURING WATER CONTENT USING SAME

FIELD OF THE INVENTION

This invention relates to an electrolytic solution for Karl Fischer's coulometric titration and a method for measuring a water content using the same.

BACKGROUND OF THE INVENTION

Karl Fischer's (hereinafter abbreviated as "KF") titration has been used widely for measurement of a water content in various samples. With the latest development of electronics, operations of apparatus for water content measurement have been made easier and simpler with increased accuracy and precision. KF titration is roughly classified into volumetric titration and coulometric titration which are carried out in different apparatus with KF reagents having different compositions suited for the respective method and apparatus.

The anolyte for KF coulometric titration (KF reagent) is composed of an iodide ion, sulfur dioxide, a basic compound, and a solvent.

KF titration is based on the following KF reaction:

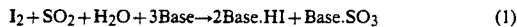

$$I_2 + SO_2 + H_2O + 3\text{Base} \rightarrow 2\text{Base}\cdot HI + \text{Base}\cdot SO_3 \quad (1)$$

(Base: basic compound)
In the anolyte for coulometric titration, iodine is supplied through electrode reaction represented by the formula:

$$2I^- \rightarrow I_2 + 2e \quad (2)$$

If water is present, iodine produced by electrolysis of formula (2) is consumed according to formula (1). On exhaustion of water, iodine becomes excessive. The end point of titration is obtained by detecting the excess of iodine. The quantity of electricity in formula (2) which has been used up to the end point is proportional to the water content.

The KF reaction of formula (1) is dependent on the pH of the system and is known to show a higher rate at a higher pH value within a certain range of pH as reported in J. C. Verhoef and E. Barendrectt, *J. Electroanal. Chem.*, Vol. 71, p.305 (1976).

The basic compound, one of components constituting the KF reagent, is required for maintaining pH within the above-mentioned certain range in which the KF reaction may proceed. To this effect, the single use of pyridine, imidazole (U.S. Pat. No. 4,378,972), triethanolamine, or morpholine (U.S. Pat. Nos. 4,429,028 and 4,740,471) has been proposed to date. However, when pyridine is used alone in a conventional electrolytic solution, the anolyte has a low pH so that the KF reaction tends to be slow, requiring slightly somewhat greater time for analysis. In using imidazole alone, the anolyte has a high pH so that the KF reaction tends to rapidly proceed, resulting in over-titration. Triethanolamine or morpholine provides too high basicity, failing to allow a normal KF reaction to proceed.

The inventors previously proposed an anolyte for KF coulometric titration which contains a mixed basic compound system comprising pyridine derivatives free from a pyridine odor as disclosed in U.S. Pat. No. 4,720,464. This anolyte achieves a higher reaction rate than in a pyridine-containing anolyte and is less causative of over-titration than with an imidazole-containing anolyte. The mixed basic compound system proposed is a mixture of an aminopyridine derivative, e.g., 4-dimethylaminopyridine and 2-methylaminopyridine, and a pyridine derivative having two pyridine nuclei linked via an alkylene group, e.g., 1,3-di(4-pyridyl)propane and 1,3-di(2-pyridyl)propane.

However, the reduction in time of analysis achieved with the above-described electrolytic solution is still insufficient. Moreover, this electrolytic solution is usable only as an anolyte, still needing further improvement so as to have such a broadened application both as an anolyte and as a catholyte, as has been recently advanced in the art.

On the other hand, chlorine-containing solvents used in most conventional titration reagents, such as carbon tetrachloride and chloroform, are not deemed suitable from the standpoint of environmental conservation. It has therefore been demanded to develop a titration reagent which is free from chlorine and still exhibits satisfactory performance.

SUMMARY OF THE INVENTION

An object of the present invention is to provide an electrolytic solution for KF coulometric titration, which is free from a pyridine odor, applicable either as an anolyte or as a catholyte, and capable of considerably reducing the time required for water content measurement.

Another object of the present invention is to provide a method for measuring a water content using such an electrolytic solution.

Other objects and effects of the present invention will be apparent from the following description.

The present invention relates to an electrolytic solution for KF coulometric titration comprising an iodide ion, sulfur dioxide, a basic compound, and a solvent, the basic compound being a mixture comprising an amino alcohol and a compound represented by formula (I):

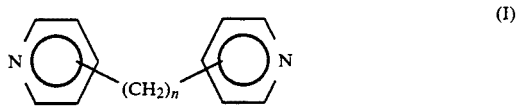

wherein n represents an integer of from 1 to 3, the amino alcohol being present at a molar ratio of not more than 1 to sulfur dioxide, and the basic compound comprising an amino alcohol and compound represented by formula (I) being present at a total molar ratio of from 1 to 5 to sulfur dioxide, and a method for measuring water content using the same.

DETAILED DESCRIPTION OF THE INVENTION

The amino alcohol which can be used as a basic compound is not particularly limited as long as it is an amine derivative containing an alcoholic hydroxyl group. Examples of the amino alcohols include mono-, di- or tri-lower alkanolamine, e.g., monoethanolamine, diethanolamine and triethanolamine, with diethanolamine being preferred. The basic compound can be a mixture comprising diethanolamine and 1,3-di(4-pryidyl) propane.

The term "lower alkanol", "lower alcohol" and the like used herein means those having from 1 to 4 carbon atoms.

Another basic compound which can be used in the present invention is a compound represented by formula (I) shown above. In formula (I), n is an integer of from 1 to 3, and is preferably 3.

Specific examples of the compound of formula (I) include 1,3-di(4-pyridyl)propane and 1,3-di(2-pyridyl)propane.

If the compound of formula (I) is used alone as a sole basic compound, because the basicity of the compound is somewhat low, the prepared electrolytic solution for KF coulometric titration gives off an irritant smell of sulfur dioxide and attains a reduced reaction rate. These disadvantages are eliminated by using the amino alcohol in combination. Such a combined use of basic compounds not only brings about improvements in odor and reaction rate but makes the resulting electrolytic solution usable either as an anolyte or as a catholyte.

In the present invention, concentration of the amino alcohol is of importance. It is required that the molar ratio of amino alcohol to sulfur dioxide should not exceed 1. The amino alcohol to sulfur dioxide molar ratio is preferably selected from a range of from 0.3 to 0.9.

If the amino alcohol to sulfur dioxide molar ratio exceeds 1, the resulting electrolytic solution for KF coulometric titration becomes strongly basic, failing to allow a normal KF reaction to proceed.

The total concentration of the amino alcohol and the compound of formula (I) with respect to sulfur dioxide is also important. A molar ratio of the sum of the basic compounds to sulfur dioxide must be from 1 to 5, and preferably from 1.2 to 3.

The electrolytic solution according to the present invention further contains an iodide ion as an essential component, either in the form of iodine or in the form of an iodide. Preferred examples of the iodides include hydroiodic acid, potassium iodide, and sodium iodide. The iodide ion concentration in the electrolytic solution generally ranges from 0.01 to 1M, and preferably from 0.03 to 0.3M.

The electrolytic solution according to the present invention furthermore contains sulfur dioxide as an essential component. The concentration of sulfur dioxide as the well as basicity of the basic compounds used greatly influence the reaction rate. Even with basic compounds of small basicity, an increased reaction rate can be assured by increasing the sulfur dioxide concentration. The sulfur dioxide concentration in the electrolytic solution ranges generally from 0.05 to 5.0M, and preferably from 0.1 to 3.0M.

Solvents which can be used in the present invention include those commonly employed in electrolytic solutions for KF coulometric titration, such as alcohols. Lower aliphatic alcohols, e.g., methanol, ethanol, isopropanol, n-butanol, isobutanol and t-butanol, are generally employed. In addition, lower alkylene glycols, e.g., ethylene glycol and propylene glycol; ethylene glycol mono-lower alkyl ethers, e.g., ethylene glycol monomethyl ether and ethylene glycol monoethyl ether; and propylene glycol mono-lower alkyl ethers, e.g., 1-methoxy-2-propanol, are also employable. The concentration of the solvent in the electrolytic solution preferably ranges from 30 to 70% by weight.

For the purpose of improving solubility of a sample to be measured, auxiliary solvents, e.g., chloroform, xylene, toluene, N-methylpyrrolidone, 2-pyrrolidone, 1,3-dimethyl-2-imidazolidinone, tetrahydrofuran and propylene carbonate, may be used in combination. These auxiliary solvents are preferably used in an amount of from 10 to 50% by weight based on the total amount of the solution.

It should be noted that chlorine-containing solvents, e.g., carbon tetrachloride and chloroform, which have been used in most conventional titration reagents, are not suitable for use from the viewpoint of environmental conservation.

The electrolytic solution according to the present invention is useful for measurement of a water content in various substances, such as organic compounds, inorganic compounds, petroleum, petrochemical products, and the like.

The method for measuring a water content using the electrolytic solution of the present invention can be carried out in a known manner. That is, the electrolytic solution of the present invention is put in an anode chamber, and the electrolytic solution of the present invention or any appropriate catholyte is put in a cathode chamber. Electricity is passed therethrough to previously remove a water content in the anolyte. Then, a sample to be measured is added to the anolyte, and an electric current is passed therethrough to titrate the water content in the sample. Where the anolyte is prepared by using iodine, water is added before analyzing the sample until the iodine color disappears.

Examples of catholytes that may be used in place of the electrolytic solution of the present invention include a mixture comprising methanol, carbon tetrachloride, sulfur dioxide, and 4-dimethylaminopyridine. In cases where use of carbon tetrachloride should be avoided in view of environmental conservation, it is recommended to use a catholyte comprising a solution of an inorganic or organic salt in at least one of lower alcohols and alkylene glycol monoalkyl ethers.

Examples of the inorganic salts include a hydrohalogenide, nitrate or perchlorate of an alkali metal, an alkaline earth metal or ammonia. Examples of the alkali metals include lithium, sodium, and potassium, with lithium being preferred. Specific examples of such an inorganic salt include ammonium chloride, lithium chloride, lithium nitrate, and sodium perchlorate, with lithium chloride being preferred.

Examples of usable organic salts include at least one selected from the group consisting of a hydrohalogenide, nitrate, perchlorate or quaternary compounds of amines and guanidine compounds.

Examples of the amines in the organic salts include those represented by formula (II):

$$R^1R^2R^3N \qquad (II)$$

wherein $R^1$, $R^2$ and $R^3$, which may be the same or different, each represents a hydrogen atom, an alkyl group having from 1 to 4 carbon atoms, or a mono- or polysubstituted alkyl group having from 1 to 4 carbon atoms (e.g., hydroxyalkyl), provided that $R^1$, $R^2$ and $R^3$ do not simultaneously represent hydrogen atoms.

The quaternary compounds can be obtained by reacting trialkylamines, etc., with alkyl iodides in a usual manner.

Specific examples of the organic salts include tetramethylammonium chloride, tetraethylammonium chloride, triethylamine hydrochloride, diethylamine hydrochloride, and choline chloride. Preferred of them are tetramethylammonium chloride and tetraethylammonium chloride. Guanidium hydrochloride is preferred as guanidium salt.

Examples of the solvents for the catholyte include those selected from the group consisting of lower alcohols having from 1 to about 4 carbon atoms, e.g., methanol, ethanol and propanol, and alkylene glycol monoalkyl ethers represented by formula (III):

$$HOR_aOR_b \qquad (III)$$

wherein $R_a$ represents an alkylene group, e.g., ethylene and propylene; and $R_b$ represents a lower alkyl group, e.g., methyl, ethyl, propyl and butyl.

These solvents may be used either individually or in combination of two or more thereof. In particular, methanol, ethylene glycol monomethyl ether, and a mixture thereof are preferred.

The concentration of the inorganic or organic salt in the catholyte ranges generally from 0.01 to 1 mol/l, and preferably from 0.1 to 0.5 mol/l.

The present invention is now illustrated in greater detail with reference to the following Examples, but it should be understood that the present invention is not construed as being limited thereto. All the percents are by weight unless otherwise indicated.

Example 1 was also used as a catholyte. The results of measurements are shown in Table 1.

COMPARATIVE EXAMPLE 1

Water content measurements were made in the same manner as in Example 1, except that a commercially available anolyte/catholyte reagent (Art. 9255, produced by E. Merck, Darmstadt) was used as an anolyte and a catholyte. The results of measurements are shown in Table 1. Art. 9255 used here contains about 1.2 mole/l of guanidine benzoate as an amine.

COMPARATIVE EXAMPLE 2

Water content measurements were made in the same manner as in Example 2, except for replacing diethanolamine with 8.9 g of 4-dimethylaminopyridine. The results obtained are shown in Table 1.

COMPARATIVE EXAMPLE 3

Water content measurements were made in the same manner as in Example 2, except for replacing 1,3-di(4-pyridyl)-propane with 8.7 g of 1,3-di(2-pyridyl)propane and replacing diethanolamine with 8.9 g of 4-dimethylaminopyridine. The results obtained are shown in Table 1.

TABLE 1

| Run No. | Example 1 (μg) | Example 2 (μg) | Comparative Example 1 (μg) | Comparative Example 2 (μg) | Comparative Example 3 (μg) |
|---|---|---|---|---|---|
| 1 | 10032.4 | 9972.9 | 10129.0 | 10455.2 | 10396.4 |
| 2 | 9766.5 | 10056.7 | 10357.2 | 10634.4 | 10390.9 |
| 3 | 9932.0 | 9961.6 | 10427.2 | 10982.7 | 10685.3 |
| 4 | 9957.8 | 10170.4 | 10449.9 | 11133.6 | 11182.7 |
| 5 | 9885.4 | 9932.0 | 10364.7 | — | 11650.1 |
| 6 | 9912.5 | 9858.6 | 10404.5 | — | 12306.0 |
| 7 | 9904.0 | 9882.6 | 10270.3 | — | — |
| 8 | 9969.0 | 9880.6 | 10318.3 | — | — |
| 9 | 10019.1 | 9836.9 | 10303.2 | — | — |
| 10 | 9854.8 | 9977.3 | 10198.1 | — | — |
| Average | 9923.4 | 9953.0 | 10322.2 | | |
| Coefficient of Variation | 0.79% | 1.02% | 0.98% | | |
| Time | 7'00"–7'20" | 7'00"–8'10" | 8'50"–11'40" | | 8'00"–16'00" |

EXAMPLE 1

A solution consisting of 8.7 g of 1,3-di(4-pyridyl)-propane, 7.6 g of diethanolamine, 5.1 g of sulfur dioxide, 20 g of 1,3-dimethyl-2-imidazolidinone, 0.95 g of iodine, and methanol as the balance to make 100 ml was used as an anolyte. A solution consisting of 65% by weight of methanol, 20% by weight of carbon tetrachloride, 5% by weight of sulfur dioxide, and 10% by weight of 4-dimethylaminopyridine was used as a catholyte. The anode chamber and the cathode chamber of a commercially available apparatus for water content measurement (Model CA-06, manufactured by Mitsubishi Kasei Corporation) each was filled with 100 ml of the anolyte and 5 ml of the catholyte, respectively. In a titration vessel was put 10 μl of water by means of a micro syringe, and water content measurements were made in accordance with the instructions for the apparatus. The measurements were repeated 10 times by using the same electrolytes. The results obtained are shown in Table 1 below.

EXAMPLE 2

Water content measurements were made in the same manner as in Example 1, except that the anolyte used in

EXAMPLE 3

A solution consisting of 8.7 g of 1,3-di(4-pyridyl)-propane, 7.6 g of diethanolamine, 5.1 g of sulfur dioxide, 10 g of 1,3-dimethyl-2-imidazolidinone, 12 g of propylene carbonate, 0.95 g of iodine, and methanol as the balance to make 100 ml was used as an anolyte. A solution of 54.8 mg of tetramethylammonium chloride dissolved in methanol to make 5 ml was used as a catholyte. Water content measurements were conducted in the same manner as in Example 1, except for using these electrolytic solutions. The results obtained are shown in Table 2 below.

COMPARATIVE EXAMPLE 4

Water content measurements were made in the same manner as in Example 3, except that a commercially available electrolyte (Aquamicron A, produced by Mitsubishi Kasei Corporation) was used as an anolyte. The results of measurements are shown in Table 2. Aquamicron A used here contains pyridine as a basic compound.

TABLE 2

| Run No. | Example 3 | Example 4 |
| --- | --- | --- |
| 1 | 9924.1 μg | unmeasurable |
| 1 | 10048.8 | |
| 3 | 9797.6 | |
| 4 | 10036.0 | |
| 5 | 9979.3 | |
| 6 | 9909.1 | |
| 7 | 10003.0 | |
| 8 | 9923.1 | |
| 9 | 10003.1 | |
| 10 | 10012.6 | |
| Average | 9963.7 | |
| Coefficient of Variation | 0.76% | |
| Time | 7'00"–7'20" | |

While the invention has been described in detail and with reference to specific examples thereof, it will be apparent to one skilled in the art that various changes and modifications can be made therein without departing from the spirit and scope thereof.

What is claimed is:

1. An electrolytic solution for Karl Fischer's coulometric titration comprising an iodide ion, sulfur dioxide, a basic compound, and a solvent, said basic compound being a mixture comprising an amino alcohol and a compound represented by formula (I):

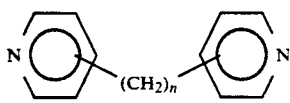

wherein n represents an integer of from 1 to 3, said amino alcohol being present at a molar ratio of not more than 1 to sulfur dioxide, and said basic compound being present at a total molar ratio of from 1 to 5 to sulfur dioxide, wherein said amino alcohol is mono-, di- or tri-lower alkanolamine.

2. An electrolytic solution for Karl Fischer's coulometric titration as claimed in claim 1, wherein said amino alcohol is monoethanolamine, diethanolamine or triethanolamine.

3. An electrolytic solution for Karl Fischer's coulometric titration as claimed in claim 1, wherein said amino alcohol is diethanolamine.

4. An electrolytic solution for Karl Fischer's coulometric titration as claimed in claim 1, wherein said compound represented by formula (I) is a compound wherein n is 3.

5. An electrolytic solution for Karl Fischer's coulometric titration as claimed in claim 1, wherein said compound represented by formula (I) is 1,3-di(4-pyridyl)propane.

6. An electrolytic solution for Karl Fischer's coulometric titration as claimed in claim 1, wherein said basic compound is a mixture comprising diethanolamine and 1,3-di(4-pyridyl)propane.

7. An electrolytic solution for Karl Fischer's coulometric titration as claimed in claim 1, wherein the molar ratio of said amino alcohol to sulfur dioxide is from 0.3 to 0.9.

8. An electrolytic solution for Karl Fischer's coulometric titration as claimed in claim 1, wherein the molar ratio of said mixture to sulfur dioxide is from 1.2 to 3.

9. An electrolytic solution for Karl Fischer's coulometric titration as claimed in claim 1, wherein said iodide ion is derived from iodine or a iodide.

10. An electrolytic solution for Karl Fischer's coulometric titration as claimed in claim 9, wherein said iodide is hydroiodic acid, potassium iodide or sodium iodide.

11. An electrolytic solution for Karl Fischer's coulometric titration as claimed in claim 1, wherein said iodide ion is present in said electrolytic solution in a concentration of from 0.01 to 1M.

12. An electrolytic solution for Karl Fischer's coulometric titration as claimed in claim 1, wherein said solvent comprises at least one member selected from the group consisting of a lower aliphatic alcohol, lower alkylene glycol, ethylene glycol mono-lower alkyl ether, and a propylene glycol mono-lower alkyl ether.

13. An electrolytic solution for Karl Fischer's coulometric titration as claimed in claim 12, wherein said solvent further comprises an auxiliary solvent selected from the group consisting of chloroform, xylene, toluene, N-methylpyrrolidone, 2-pyrrolidone, 1,3-dimethyl-2-imidazolidinone, tetrahydrofuran and propylene carbonate.

14. A method for measuring a water content in a sample by Karl Fischer's coulometric titration, in which an electrolytic solution is used as an anolyte, or catholyte or the anolyte and the catholyte, said electrolytic solution comprising an iodide ion, sulfur dioxide, a basic compound, and a solvent, said basic compound being a mixture comprising an amino alcohol and a compound represented by formula (I):

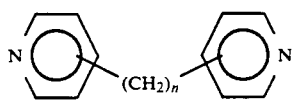

wherein n represents an integer of from 1 to 3, said amino alcohol being present at a molar ratio of not more than 1 to sulfur dioxide, and said basic compound being present at a total molar ratio of from 1 to 5 to sulfur dioxide.

15. A method as claimed in claim 14, wherein said electrolytic solution is used as an anolyte.

16. A method as claimed in claim 14, wherein said electrolytic solution is used as both a catholyte and an anolyte.

17. A method as claimed in claim 14, wherein said electrolytic solution is used as an anolyte and a solution of an inorganic or organic salt in at least one solvent selected from a lower alcohol and an alkylene glycol monoalkyl ether is used as a catholyte.

18. A method as claimed in claim 17, wherein said inorganic salt is a hydrohalogenide, nitrate or perchlorate of an alkali metal, an alkaline earth metal or ammonia.

19. A method as claimed in claim 17, wherein said inorganic salt is ammonium chloride, lithium chloride, lithium nitrate, or sodium perchlorate.

20. A method as claimed in claim 17, wherein said inorganic salt is lithium chloride.

21. A method as claimed in claim 17, wherein said organic salt is at least one selected from the group consisting of a hydrohalogenide, nitrate, perchlorate and quaternary compound of amines and guanidine compounds.

22. A method as claimed in claim 17, wherein said amine is a salt of an amine represented by formula (II):

$$R^1R^2R^3N \qquad (II)$$

wherein $R^1$, $R^2$ and $R^3$, which may be the same or different each represent a hydrogen atom, an alkyl group having from 1 to 4 carbon atoms, or a mono- or ply-substituted alkyl group having from 1 to 4 carbon atoms, provided that $R^1$, $R^2$ and $R^3$ do not simultaneously represent hydrogen atoms.

23. A method as claimed in claim 17, wherein said organic salt is tetramethylammonium chloride, tetraethylammonium chloride, triethylamine hydrochloride, diethylamine hydrochloride, choline chloride, or guanidium hydrochloride.

24. A method as claimed in claim 17, wherein said organic salt is tetramethylammonium chloride or tetraethylammonium chloride.

25. A method as claimed in claim 17, wherein said solvent comprises a lower alcohol having from 1 to 4 carbon atoms.

26. A method as claimed in claim 17, wherein said solvent comprises an alkylene glycol monoalkyl ether represented by formula (III):

$$HOR_aOR_b \qquad (III)$$

wherein $R_a$ represents an alkylene group; and $R_b$ represents a lower alkyl group.

27. A method as claimed in claim 25, wherein said lower alcohol is methanol.

28. A method as claimed in claim 26, wherein said alkylene glycol monoalkyl ether is ethylene glycol monomethyl ether.

29. A method as claimed in claim 17, wherein said solvent comprises a mixture of a lower alcohol and an alkylene glycol monoalkyl ether.

* * * * *